United States Patent [19]

Volk

[11] Patent Number: 5,333,017
[45] Date of Patent: Jul. 26, 1994

[54] INDIRECT OPHTHALMOSCOPY LENS FOR USE WITH SLIT LAMP BIOMICROSCOPE

[76] Inventor: Donald A. Volk, 7893 Enterprise Dr., Mentor, Ohio 44060

[21] Appl. No.: 973,988

[22] Filed: Nov. 6, 1992

[51] Int. Cl.$^5$ .......................... A61B 3/10; G02B 3/02
[52] U.S. Cl. .................................. 351/205; 359/708; 359/712
[58] Field of Search ................. 359/708, 712; 351/205

[56] References Cited

U.S. PATENT DOCUMENTS

| | | | |
|---|---|---|---|
| 3,944,341 | 3/1976 | Pomerantzeff | 351/7 |
| 3,954,329 | 5/1976 | Pomerantzeff | 351/16 |
| 4,134,647 | 1/1979 | Ramos-Caldera | 351/6 |
| 4,410,245 | 10/1983 | Koester | 351/219 |
| 4,452,514 | 6/1984 | Spitznas | 351/206 |
| 4,469,413 | 9/1984 | Shirayanagi | 350/432 |
| 4,502,764 | 3/1985 | Riquin | 351/160 R |
| 4,627,694 | 12/1986 | Volk | 351/214 |
| 4,669,839 | 6/1987 | Muchel | 351/221 |
| 4,704,018 | 11/1987 | Takhashi | 351/206 |
| 4,721,378 | 1/1988 | Volk | 351/205 |
| 4,728,183 | 3/1988 | Heacock et al. | 351/219 |
| 4,738,521 | 4/1988 | Volk | 351/205 |
| 5,007,729 | 4/1991 | Erickson et al. | 351/219 |
| 5,046,836 | 9/1991 | Volk | 351/219 |

OTHER PUBLICATIONS

G. El Bayadi, "New Method of Slit-Lamp Micro-Ophthalmoscopy", (1953), pp. 625–628, Brit. J. Ophthal.
R. David Sudarsky, M.D. et al, "Aspherical Objective Lenses", (1959), pp. 572–575, American Journal of Ophthalmology, vol. 47, No. 4.

*Primary Examiner*—Loha Ben
*Assistant Examiner*—Thomas Robbins
*Attorney, Agent, or Firm*—Oldham, Oldham & Wilson Co.

[57] ABSTRACT

The lens of the invention is specifically designed for use with a slit lamp biomicroscope in the examination of a patient's eye. One or more lens elements may be used with each lens element having first and second convex aspheric surfaces of revolution. The first and second aspheric surfaces are coaxial and non-symmetrical with respect to one another. The aspheric surfaces are chosen to correct astigmatic imagery of the lens, with the formed aerial image free of excessive field curvature and astigmatism. The lens is held at a distance from the patient's eye pupil corresponding to the secondary focal length of the lens. If the examined eye is emmetropic, and the lens is held in a position wherein the entrance pupil of the lens is conjugate with that of the examined eye, an image of the entrance pupil of the patient's eye will be formed at the pupil aperture of the optical system of the slit lamp biomicroscope used to observe the aerial image of the fundus as produced by the lens. The ratio of the apical radius of curvature of each surface and the ratio of the apical eccentricities of each surface are chosen to optimally correct for astigmatic imagery as well as pupil imagery of the lens, being dependent upon the index of refraction of the optical quality glass or plastic used in the production of such lenses. The indirect ophthalmoscopy lens of the invention therefore provides a sharper, focused fundus image and extremely wide field of view by optimally correcting for the primary image quality of the lens, as determined by astigmatism and image flatness, as well as the spherical aberration of the conjugate pupil image, specific to the pupil of the objective lens system of the observing slit lamp biomicroscope.

19 Claims, 5 Drawing Sheets

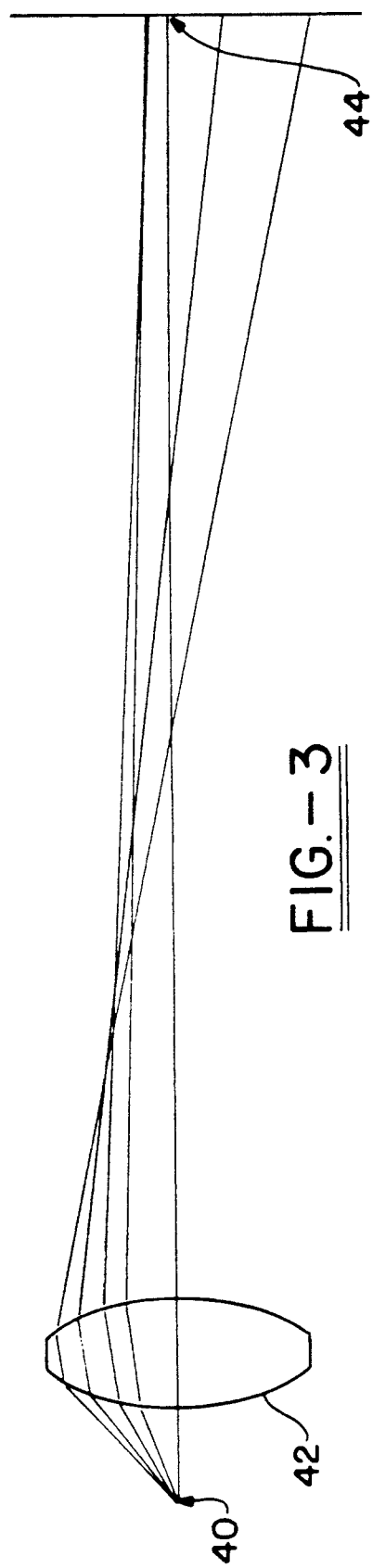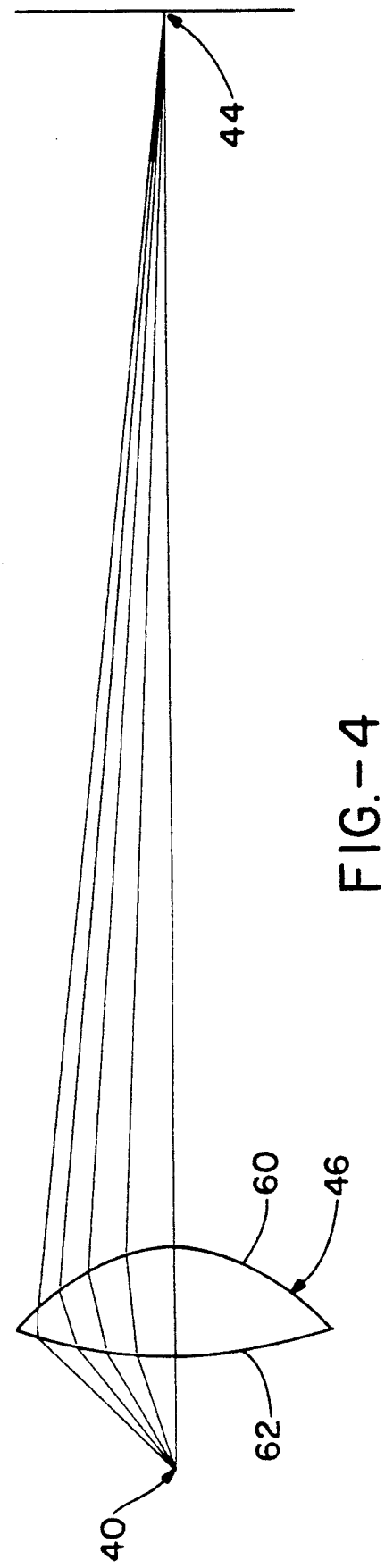

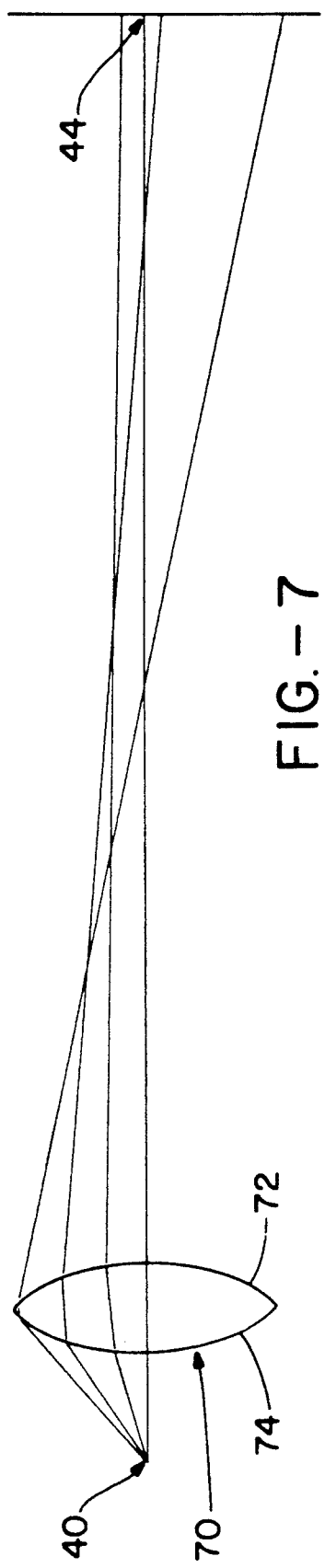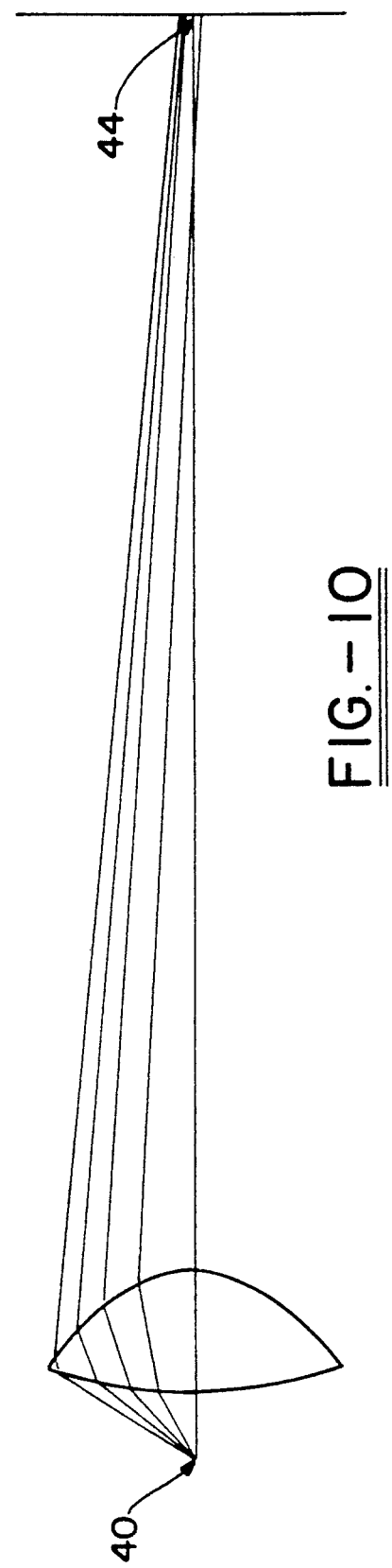
FIG.-7
FIG.-10

INDIRECT OPHTHALMOSCOPY LENS FOR USE WITH SLIT LAMP BIOMICROSCOPE

TECHNICAL FIELD

This invention relates generally to an improvement in an indirect ophthalmoscopy lens specifically designed for examination or treatment of the fundus of the eye by means of a slit lamp or other biomicroscope. The optical lens functions both as a condensing lens for converging light from the slit lamp biomicroscope light source into the eye to illuminate the fundus of the eye, and as an image-forming lens adapted to form an aerial image of the fundus of the eye which is viewed with the slit lamp biomicroscope. More particularly, the invention relates to an improved indirect ophthalmoscopy lens for use with a slit lamp biomicroscope, the lens providing an extremely wide field of view and better image resolution, particularly at the peripheral regions of the formed image. The lens is particularly adapted for use with the slit lamp microscope, wherein the quality of the imagery of the eye pupil of the examined eye conjugate with the slit lamp biomicroscope "pupil" is optimized along with correction of the primary image quality. In this manner, the image-forming qualities of the lens remain optimized while the viewability of the formed image using the binocular microscope of the slit lamp or other instrument is enhanced.

BACKGROUND OF THE INVENTION

Indirect ophthalmoscopy techniques are now in widespread use in diagnostic and therapeutic procedures in the field of ophthalmology. Indirect ophthalmoscopy techniques include the use of a hand-held lens, in conjunction with a binocular indirect ophthalmoscope, and more recently in biomicroscopic examination of the fundus using a slit lamp biomicroscope. The so-called hand-held condensing lens used in indirect ophthalmoscopy performs two functions: condensing the light from the source toward the entrance pupil of the eye, thereby illuminating the fundus, and forming an inverted real aerial image of the fundus at approximately the front focal distance of the lens. It has been found that indirect ophthalmoscopy is superior to direct ophthalmoscopy in the examination of retinopathies, retinal separation, retinal tumors, intraocular foreign bodies, and further in the ability to see fundus lesions which may not be viewable if there are opacities of the ocular media. The hand-held lenses used in indirect ophthalmoscopy have been of a variety of types, with each affording some advantages in the examination of the fundus.

The first hand-held indirect ophthalmoscopy lens which was used as a condensing and image-forming lens, included convex spherical surfaces and was of low power. The aerial image produced with such a spherical lens was magnified and inverted, but was quite blurred, particularly toward the periphery of the formed image. Subsequently, improvements were noted by the use of slightly higher powered lenses, each having one aspheric surface with the other surface being plano or spherical. Although the use of an aspherical surface in the indirect ophthalmoscopy lenses does show great improvement over spherical indirect ophthalmoscopy lenses, lens aberrations may remain such that light from the light source is not converged to a sharply defined image at the entrance pupil of the eye, and the formed aerial image of the fundus may show aberrations and increasing astigmatic effects particularly toward the periphery of the formed image. These designs were subsequently improved upon with the use of two aspherical surfaces incorporated into the indirect ophthalmoscopy lens. The first use of a double aspheric indirect ophthalmoscopy lens, designed for use with the indirect ophthalmoscope was described in U.S. Pat. No. 4,738,521, by David Volk, wherein a lens for use in indirect ophthalmoscopy had both the front and back surfaces of the lens being aspheric surfaces of revolution of conoid type. This double aspheric lens substantially improved the aerial image formed and reduced aberrations of the image including field curvature, astigmatism, and distortion. The use of double aspheric lenses, wherein the surfaces are particularly conoid surfaces, has been found to be of distinct advantage in indirect ophthalmoscopy and has made possible in use of much stronger lenses while providing increased clarity of the image with increased size of the field of view.

More recently, there has been developed a symmetrical double aspheric indirect ophthalmoscopy lens particularly suited for use with the slit lamp biomicroscope. This lens is described in U.S. Pat. No. 4,627,694, also by David Volk. The symmetrical double aspheric lenses as shown in this patent are of small diameter, with the aspheric surfaces described as having decreasing curvature from the apices of the surfaces peripheralward, and providing improved correction of aberrations including field curvature, astigmatism, and distortion. Lenses made according to this design have demonstrated themselves to be better suited for use with the slit lamp biomicroscope and have yielded significant improvement in the examiner's ability to see details in the aerial image of the fundus, yet the lens design does not account for pupil aberrations, which may be inherent in the lens design and which degrade the optical and performance characteristics of a lens, especially as it relates to observation of the fundus image using the slit lamp biomicroscope. Similarly, other prior indirect ophthalmoscopy lenses have apparently neglected completely the effects of pupil aberration in their design.

Particular problems arise when attempting to use a slit lamp biomicroscope for viewing of the aerial image formed by an indirect ophthalmoscopy lens. If the lens is of lower power, the beam of light from the slit lamp light source associated with the biomicroscope cannot be enlarged sufficiently to fill the full aperture of the lens, leaving a considerable portion of the lens unused in its condensing function. With the development of the double aspheric indirect ophthalmoscopy lenses described above, this problem was overcome by enabling the use of higher powered lenses, allowing greater illumination of the fundus and increased field of view. Although such lens design improvements have played an important role in present day eye fundus diagnostic and therapeutic techniques, especially with respect to diagnosis of diseases of the vitreous and retina, there has not been developed an indirect ophthalmoscopy lens particularly designed for use with a slit lamp biomicroscope, which optimally corrects for pupil aberrations as well as the more commonly considered aberrations, field curvature, astigmatism, and distortion and as such provides an extremely wide field of view and achieves very high resolution of the image even at peripheral portions thereof.

An indirect ophthalmoscopy lens for use with a slit lamp biomicroscope must also be positioned relative to the patient's eye, such that the conjugate focus of the slit lamp light source through the lens is at approximately the center of the entrance pupil of the patient's eye. The lens must thus be positioned a sufficient distance from the entrance pupil to form the conjugate focus of the slit lamp light source at the proper position for greatest illumination of the fundus. For higher powered lenses, the lens is positioned relatively close to the front of the patient's cornea, while the microscope of the slit lamp is positioned at a significant distance from the patient in order to allow observation of the formed aerial image of the fundus. The distance from the aerial image to the biomicroscope apparatus is dependent upon the attributes of the slit lamp microscope and particularly the focal distance of the objective lens system of the microscope. For the purpose of providing a wider field of view of the fundus by means of slit lamp ophthalmoscopy, the particular diameters of the more highly powered prior art lenses have been made relatively large, such that light rays originating at the more peripheral portions of the illuminated fundus, proceeding through the pupil and cornea, are incident upon the posterior lens surface at its periphery. Although refracted through the lens and contributing to the aerial image formation, these peripheral rays, as a result of inadequate lens design, in fact do not provide peripheral fundus imagery to the practitioner viewing through the slit lamp biomicroscope. This is due to the pupil aberrations of the indirect ophthalmoscopy lens, and the fact that the lens design has not addressed the optical characteristics and requirements of the slit lamp biomicroscope itself. It is therefore seen that the field of view and the image quality obtainable by prior art indirect ophthalmoscopy lenses has not been optimized for examination using a slit lamp microscope, the quality of the imagery of the eye pupil as it specifically relates to the slit lamp microscope pupil having been completely neglected. If the indirect ophthalmoscopy lens has significant pupil aberration, there will be excess vignetting of light rays, even at the mid-peripheral portions of the field of view. In certain cases, the rays from the edge of the field of view may completely miss the objective of the slit lamp microscope. Additionally, as previously stated, the illuminating system of the slit lamp biomicroscope is such that light from the slit lamp light source is reflected and converged to form a real aerial image of the slit lamp light source between the reflecting surface of the microscope and the indirect ophthalmoscopy lens. As the hand-held indirect ophthalmoscopy lens should be positioned in front of the patient's eye at a location which provides that the conjugate focus of the slit lamp source is at or near the center of the entrance pupil of the patient's eye, the slit lamp light source is relatively close to the indirect lens. The quality of the imagery of the eye pupil into the slit lamp microscope "pupil" will also be dependent upon such positioning, and again excess pupil aberrations may result in less than desired illumination of the eye fundus.

SUMMARY OF THE INVENTION

Based upon the foregoing, there has been found a need to provide a hand-held indirect ophthalmoscopy lens, wherein the condensing and image-forming functions, as well as the pupil characteristics of the lens are optimized for examination using the slit lamp biomicroscope.

The lens of the invention is specifically designed for use with a slit lamp biomicroscope in the examination of a patient's eye. One or more lens elements may comprise the indirect ophthalmoscopy lens of this invention. Each lens element is made of homogenous transparent optical material and has first and second convex aspheric surfaces of revolution. The first and second aspheric surfaces are coaxial and non-symmetrical with respect to one another. The magnitude and shape of each of the first and second aspheric surfaces is defined by the polynomial:

$$y = (2rx + (e^2 - 1)x^2)^{\frac{1}{2}} + Ax^F + Bx^G + Cx^H;$$

where r equals the apical radius of curvature of each surface, e equals the apical eccentricity of each surface, and co-efficients A, B, and C equal successive terms in the polynomial, and F, G, and H equal exponents in the successive terms. The aspheric surfaces are chosen to correct astigmatic imagery of the lens, with the formed aerial image free of excessive field curvature and astigmatism. The lens is adapted to be hand held, and in the preferred embodiment includes a supporting housing which enables the lens to be held at a distance from the patient's eye pupil corresponding to the back focal length of the lens. If the examined eye is emmetropic, and the lens is held in a position wherein the entrance pupil of the lens is conjugate with that of the examined eye, an image of the entrance pupil of the patient's eye will be formed at the pupil aperture of the optical system of the slit lamp biomicroscope used to observe the aerial image of the fundus as produced by the lens. The ratio of the apical radius of curvature of each surface and the ratio of the apical eccentricities of each surface are chosen to optimally correct for astigmatic imagery as well as pupil imagery of the lens, being dependent upon the index of refraction of the optical quality glass or plastic used in the production of such lenses. The indirect ophthalmoscopy lens of the invention therefore provides a sharper, focused fundus image and extremely wide field of view by optimally correcting for the primary image quality of the lens, as determined by astigmatism and image flatness, as well as the spherical aberration of the conjugate pupil image, specific to the pupil of the objective lens system of the observing slit lamp biomicroscope.

BRIEF DESCRIPTION OF THE DRAWINGS

A better understanding of the invention will be obtained upon a further reading of the detailed description in conjunction with the drawings, wherein:

FIG. 3 shows the pupil imagery of a prior art indirect ophthalmoscopy lens;

FIG. 4 shows the pupil imagery of an indirect ophthalmoscopy lens in accordance with the invention;

FIG. 7 shows the pupil imagery of another prior art indirect ophthalmoscopy lens;

FIG. 10 shows the pupil imagery of another example of an indirect ophthalmoscopy lens in accordance with the invention;

DETAILED DESCRIPTION OF THE INVENTION

Figures 1, 2:
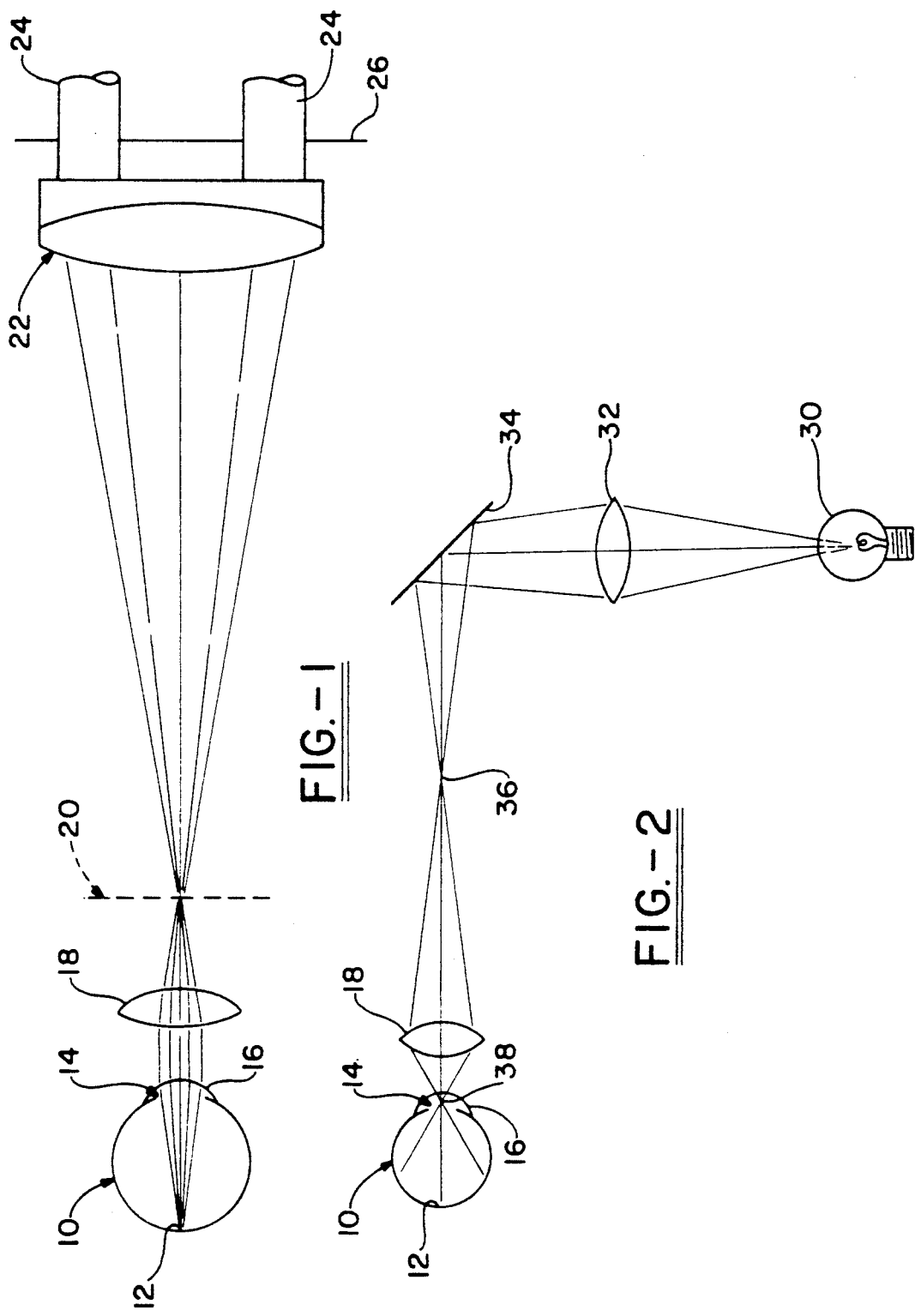
FIG. 1 is a schematic diagram of the slit lamp biomicroscope observation optical system of a typical slit lamp biomicroscope.
FIG. 2 is a schematic illustration of the illumination system used in a typical slit lamp biomicroscope.

Turning now to FIG. 1, there is shown an observing optical system for a typical slit lamp biomicroscope, wherein light from the fundus (12) of an examined eye (10) emanates from the fundus (12) through the pupil (14) of the eye (10) and outward through the cornea (16). Generally, indirect ophthalmoscopy with the slit lamp biomicroscope is performed with the pupil (14) of the examined eye (10) dilated, which permits the greatest illumination and therefore widest field of view of the fundus (12). Dilation of the pupil (14) will also facilitate binocular stereoscopic viewing of the aerial image of the fundus (14) with the slit lamp biomicroscope. Light rays emerging from points on fundus (12) are directed to an indirect ophthalmoscopy lens (18), which acts to converge the light toward an image plane (20), where it is intended that a sharp, clear, aberration-free image of the fundus will be formed. When examining an emmetropic eye, the position of image plane (20) should coincide with the anterior focal plane of the indirect ophthalmoscopy lens (18) as well as the focal plane of the slit lamp illumination beam and microscope objectives. As seen in FIG. 1, light rays emanating from the fundus (12) will continue past image plane (20) and toward the slit lamp front objective lenses (22) of a typical slit lamp microscope. The objective lenses (22) of the slit lamp microscope focus light directed from the indirect ophthalmoscopy lens (18) to a pair of eye pieces or separate ocular optical systems at (24) for binocular and stereoscopic viewing of the fundus image formed at plane (20). An objective diaphragm (26) limits light rays entering the eye pieces of the slit lamp microscope, and provides the aperture of the observation optical system. Although not distinctly shown in FIG. 1, the viewing system of the slit lamp microscope may also include in each of the binocular viewing optical systems, a Galilean telescope system, further objective lenses, reflecting prisms or mirrors as well as eye piece oculars and associated field of vision diaphragms. Although the construction of various slit lamp microscopes varies to some degree, each will include an objective lens system (22) for focusing light emerging from the indirect ophthalmoscopy lens (18) toward the individual eye pieces (24) of the microscope. The objective lens system (22) will define the "pupil" of the slit lamp microscope corresponding to the back focus of the optical system.

Although there is shown in FIG. 1 the formation of a single aerial image of the fundus which is an object for the objective lens of the biomicroscope, with binocular viewing capabilities, there are two overlapping slightly laterally displaced and slightly different aerial images which are viewed with the respective eyes of the examiner binocularly through the corresponding optics of the biomicroscope. As is well known, the two images as seen with the eyes of the examiner creates the retinal image disparity required for stereopsis.

In FIG. 2, the illumination system of a typical slit lamp microscope is also shown, which includes a light source (30) for generating illuminating light which is directed to a condenser lens (32). The light from light source (30) is converged via lens (32) toward a reflecting surface (34), such as a mirror, and reflected toward the examined eye (10). The light from source (30) is reflected from the mirror (34) is converged to form a real aerial image of the slit lamp light source at (36) between the mirror (34) and the indirect ophthalmoscopy lens (18) used in conjunction with the microscope. The indirect ophthalmoscopy lens acts as a condensing lens to form an image of the light source slightly behind the secondary focus of the lens, such that the light source and its image are conjugate. The indirect ophthalmoscopy lens (18) is thus positioned a distance from the entrance pupil (14) of the examined eye which is slightly greater than the back focus of the lens with the conjugate focus of the slit lamp light source at or near the center of the entrance pupil of the examined eye as seen at (38). In this manner, greatest illumination of the fundus (12) can be achieved, to allow a wider field of view of the formed aerial image of the fundus.

Turning to FIG. 3, there is shown a ray tracing depicting spherical aberration of the pupil as it relates to a lens such as the indirect ophthalmoscopy lens (42). This pupil aberration may be thought of as a longitudinal displacement on the optical axis of the entrance pupil as a function of field angle in the pupil imagery provided by indirect ophthalmoscopy lens (42). Refraction of light rays emanating from entrance pupil (40) by lens (42) do not converge at a point which would coincide with the "pupil" (44) of the slit lamp optics used to view the aerial image of the fundus produced by the indirect ophthalmoscopy lens (42). The eye pupil (40) is thus not correctly imaged to a conjugate point corresponding to the "pupil" of the slit lamp optics at (44), such that observation using the slit lamp microscope is impaired.

In FIG. 4, the indirect ophthalmoscopy lens of the invention (46) is shown to provide significant correction of pupil aberrations, such that rays emerging from the entrance pupil (40) of a patient's eye will be refracted by lens (46) to a focal area corresponding to the "pupil" (44) of the slit lamp observation optics. In comparison to FIG. 3, the optical characteristics of lens (46) provide for significant correction of pupil aberrations, with light rays originating at the entrance pupil (40) of the eye and incident upon peripheral regions of lens (46) contributing to image formation and observation. The rays proceed to the viewing optical system of the slit lamp microscope in such a way as to allow the widest field of view to be obtained while maintaining the substantially aberration-free image of the fundus observed through the slit lamp microscope. This feature of a hand-held indirect ophthalmoscopy lens used in conjunction with the slit lamp, relating to the quality of the imagery of the eye pupil into the slit lamp microscope pupil, has not been recognized in the prior art. If the indirect ophthalmoscopy lens has severe pupil aberrations, the overall image quality will suffer as there will be excessive vignetting of light rays at outer portions of the field of view. The pupil imagery shown in FIG. 4 can be compared with that of FIG. 3, which shows the pupil imagery for a prior art aspherical ophthalmoscopic lens produced by Nikon, having a stated power of 90.1 diopters. The pupil characteristics of this prior art lens, as seen in the ray tracing, demonstrate significant pupil aberration. It should be recognized that light rays passing through the peripheral portion of the prior art Nikon lens, while possibly contributing to image formation do not meet the requirements of good pupil imagery and conjugacy. In certain cases, rays from the edge of the field of view may completely miss the objective of the slit lamp microscope.

Taking into consideration the effects of pupil aberration, the indirect ophthalmoscopy lens of the invention functions both to correct the primary image quality of the lens, as determined by astigmatism, and also to correct the pupil imagery. Referring back to FIG. 4, the indirect ophthalmoscopy lens (46) of the invention is made of a homogenous transparent material and has a first convex aspheric surface of revolution (60) and a second convex aspherical surface of revolution (62), which together correct both primary image quality as well as pupil aberrations in lens (46). In a single-element bi-aspheric lens of this type, there are only two design variables of any significant importance which can be adjusted to correct for these aberrations, once the net lens power has been fixed. One of these variables is the lens shape, or "bending" of the lens. The desired net power of the lens, whatever it may be, can be achieved by an infinite variety of lens shapes, which differ in the power attributed to the front surface (60) and the back surface (62) of the lens. Shifting of power from one side of lens to the other provides a continuous variable in design of the lens. The other variable in design consideration, is the net amount of aspheric deformation of each of the lens surfaces. In theory, a given amount of aspheric deformation can also be divided up between the front and back surfaces of the lens. The lens shape as well as front and back eccentricity values of the novel invention are chosen based on specific design criteria.

With these two design variables, the lens shape, or "bending", and the net amount of aspheric deformation, it is possible to correct for both primary image quality as well a pupil aberrations. In the indirect ophthalmoscopy lens (46) of the invention, the primary image quality of the lens is corrected by the aspheric deformation of surfaces (60) and (62) with the particular correction balanced between the sagittal and tangential astigmatic fields being affected by both the relationships of the power of the front and back surfaces of the lens as well as the distribution of aspheric deformation on the lens surfaces. The design of lens (46) is also corrected for pupil aberrations, resulting in very good pupil imagery with respect to the slit lamp biomicroscope. For a particular net power of the lens, the design of the lens (46) provides optimum field correction as well as correction for pupil aberration, to yield a much improved lens for use with a slit lamp biomicroscope. The surfaces of the lens of the invention are non-symmetrical with respect to one another, which enables correction of both pupil and image aberrations, particularly in larger diameter lenses, which is not achievable in a symmetrical design. The magnitude and shape of each of the surfaces is defined by the polynomial expressed as follows:

$$y = (2rx + (e^2 - 1)x^2)^{\frac{1}{2}} + Ax^F + Bx^G + Cx^H;$$

where r equals the apical radius of curvature of each surface, e equals the apical eccentricity of each surface, and co-efficients A, B, and C equal successive terms in the polynomial, and F, G, and H equal exponents in the successive terms. As an example of the preferred embodiment, for a lens (46) having a focal length of 12.7 mm or net power of 78.71 diopters, and made from a glass having an index of refraction of 1.734, the apical radius of curvature, r, of the front surface (60) is 13.18 mm, with an apical eccentricity, e, of 1.053. The back surface (62) of this example has an apical radius of curvature of 21.94 mm with an apical eccentricity, e, of 4.864. The thickness of the lens (46) is 9.53 mm. Although the deformation coefficients and exponents have not been specified in this example, these parameters can be used in the lens design if desired.

In this preferred embodiment, for a lens which is positioned at a distance of 10.40 mm from the eye pupil, and forming an aerial image of the fundus at a position 10.81 mm from the anterior surface (60) of lens (46), the first to second surface power relationship is established for optimum pupil imagery. In this preferred example, the ratio of the apical radius of curvature of the first surface (62) to the second surface (62) is 1.665, which is reflective of the optimum surface to surface relationship for correcting pupil aberrations. The lens of this example, being corrected for pupil aberrations, will thus enable light rays incident upon the entire surface (62) to be converged and contribute to the formation of the aerial image which can then be optimally viewed with a slit lamp biomicroscope. It has been found that when the cone angle of the chief rays of each of the bundles of light rays emerging from the eye pupil exceeds approximately 25 degrees, it becomes increasingly important to correct for pupil aberration to enable peripheral regions of the lens to remain useful in and to obtain a very wide field of view relative to prior art lenses. The lens of this invention thus enables the full diameter of the lens to remain useful in condensing and image forming functions. This aspect of the lens is particular to use of a slit lamp biomicroscope, which typically has an objective lens system having a focal length of approximately 100 mm. This relatively long focal length will adversely effect observation of the aerial image if pupil aberration is not adequately corrected. In the lens of the invention, the chief rays at the eye pupil will be converged by the indirect ophthalmoscopy lens (46) at the "pupil" of the slit lamp optics, corresponding to the working distance of the slit lamp microscope and the focal distance of the objective lens system associated therewith. In this manner, the optimized design of the indirect ophthalmoscopy lens (46) allows the greatest latitude in lens positioning relative to the patient's eye while maintaining good optical quality, and correspondingly, also allowing a greater range of adjustment of the slit lamp microscope for examination or treatment of the eye fundus. Thus, the design of the lens for a predetermined net power may vary slightly while still achieving the desired correction of pupil aberrations and imaging characteristics of the lens, as the observer's pupil will allow some slight error in the convergence of light rays at the "pupil" of the slit lamp optics. The correction of both image and pupil aberrations, and the wider field of view obtained with this invention, facilitate a more comprehensive fundus examination and treatment up to 150° in field extent.

Figure 5:
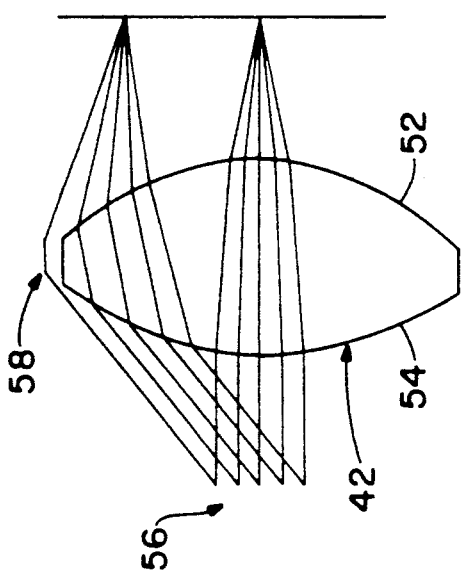
FIG. 5 shows a schematic illustration of imaging characteristics in a prior art indirect ophthalmoscopy lens.
Figure 6:
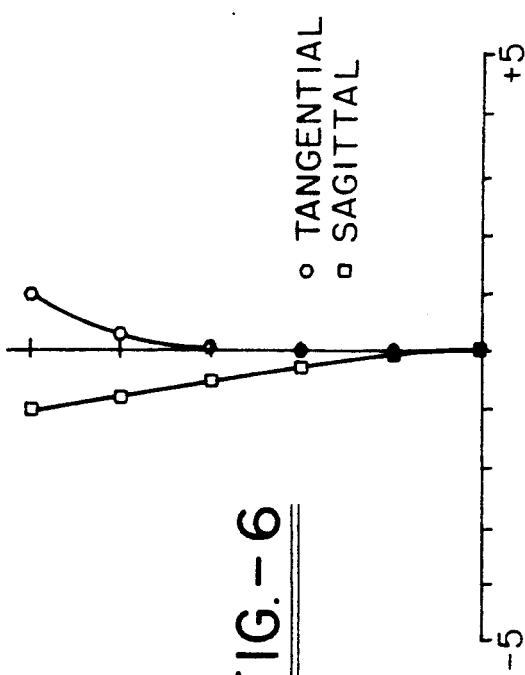
FIG. 6 shows the field curves for the prior art indirect ophthalmoscopy lens shown in FIG. 5.

Turning to FIGS. 5 and 6, the imaging characteristics and field curves of the prior art Nikon 90D lens mentioned with respect to FIG. 3 are shown. The lens (42) has a front surface (52), adapted to be positioned toward the observer, having an apical radius of curvature of approximately 9.63 mm and an apical eccentricity of 1.61 as measured with the Form Talysurf Series measuring system produced by Rank Taylor Hobson, Inc. The back surface (54) of lens (42) has an apical radius of curvature of approximately 13.61 mm, and an apical eccentricity of approximately 1.58, while the lens has a center thickness of approximately 11.08 mm and a diameter of approximately 21.95 mm. The index of refraction of the glass used for the lens has been calculated to be 1.621, based on the stated power of 90.1 diopters, thus the glass material is of a typical index of refraction for optical quality glass used for such lenses. For an eye pupil having a diameter of 5 mm as shown at (56), and a pupil to lens distance of 7.5 mm, it is noted that the imaging characteristics of the lens (42) result in vignetting of light rays for the outer parts of the field of view by the lens diameter as seen at (58). This prior art lens will form an aerial image at a position 7.64 mm from anterior surface (52), but as previously stated, light rays from the pupil are vignetted by the lens diameter, so as not to contribute to the image as seen with a slit lamp biomicroscope. The field curves for the prior art Nikon 90D lens indicate that the tangential astigmatic is well corrected, while the sagittal astigmatic field curve is slightly less well corrected. Although the field curves of the Nikon 90D lens do show that the lens is relatively well corrected for overall image quality, the lens has not been corrected for pupil aberrations as indicated in FIG. 3. The field of view and the resolution of the image observed through a slit lamp microscope will therefore be adversely effected, to result in less than optimum performance in use with a slit lamp microscope.

The pupil imagery of another prior art lens is shown in FIG. 7, which relates to a 90D lens produced by Volk Optical, Inc. The lens (70) includes two symmetrical aspheric surfaces (72) and (74), each having an apical radius of curvature of a 11.622 mm and an apical eccentricity of 1.543. The center thickness of the lens (70) is 8.763 mm, and the lens has a diameter of 21.55 mm and is constructed of a glass having an index of refraction of 1.523. The imaging characteristics of the prior art Volk 90D lens indicate that again the image aberrations have been relatively well corrected and although this lens shows better pupil characteristics than the Nikon 90D lens (as seen in FIG. 3), significant pupil aberration remains, particularly at the peripheral portions of the image. Again, although the primary image quality has been corrected to a significant degree, pupil aberrations have not been corrected, resulting in less than optimum performance for use with a slit lamp biomicroscope.

Figure 8:
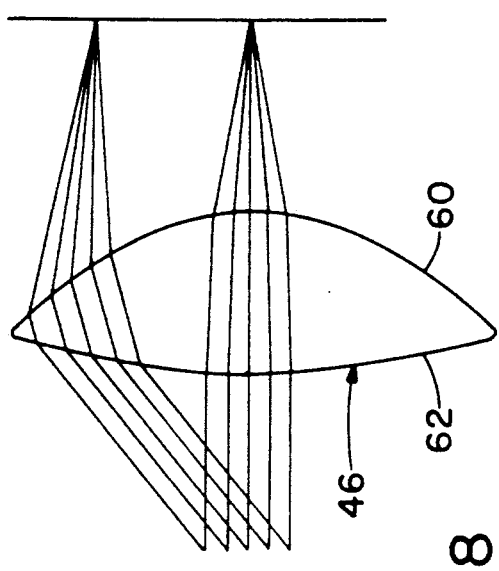
FIG. 8 shows a schematic representation of the imaging characteristics for the indirect ophthalmoscopy lens in accordance with the invention.
Figure 9:
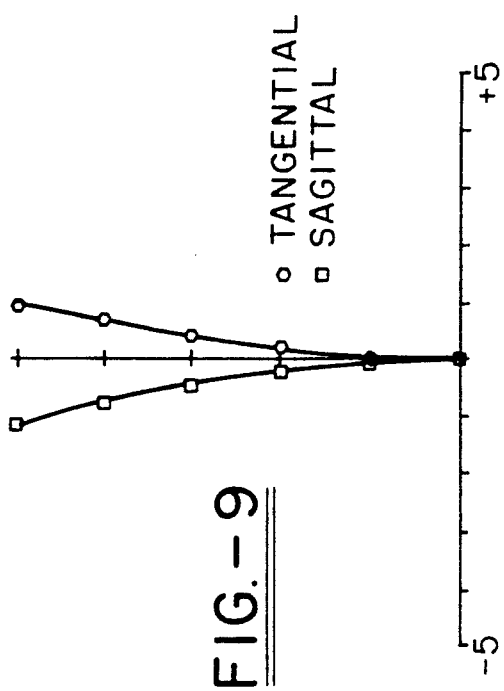
FIG. 9 shows the field curves for the indirect ophthalmoscopy lens in accordance with the invention, as shown in FIG. 8.

Turning to FIGS. 8 and 9, the imaging characteristics of the indirect ophthalmoscopy lens (46) referred to in FIG. 4, in accordance with the preferred example given above, are shown. For an eye pupil of 5 mm, and with the lens positioned 10.40 mm from the eye pupil, the imaging characteristics of lens (46) are optimized, with pupil aberrations at the "pupil" (44) of the slit lamp microscope optics being substantially eliminated (shown in FIG. 4). As seen in FIG. 10, the astigmatic field curves of the lens (46) indicate that the lens if well corrected for primary image quality, with the sagittal field being made as flat as possible while still correcting for pupil aberrations in the lens. Thus, the lens has been optimized in terms of both primary image quality as well as pupil imagery, which will greatly facilitate its use with a slit lamp biomicroscope. With the design variables of surface power and aspheric surface deformation, both aberrations affecting primary image quality and pupil aberrations are corrected in a unique set of parameters for a lens of a given power. The characteristics of the lens may change if the index of refraction of the lens glass or plastic is modified, the center thickness is independently changed, or if the net lens power is changed. When it is desired to obtain a fundus image of greater or lesser magnification in order to facilitate a more comprehensive fundus diagnosis, the system focal length or dioptric power must be appropriately changed. To obtain a fundus image of greater actual size, a lens of lower power may be utilized and conversely to obtain a very wide field fundus image of decreased actual size, a lens of higher power may be used. With maximum potential field of view kept at a constant for lens powers ranging from 50 to 150 diopters, it has been found that the surface to surface radii relationship and surface to surface eccentricity relationship remains essentially constant in the optimization of the lens design. Whether a high or lower power lens is considered within the 100 diopter range mentioned, other than a change in diameter, center thickness, and surface vertex radii, the front to back radii ratio will remain essentially identical to the already proposed model, as will the front to back eccentricity ratio and actual eccentricity values. Slight modifications in eccentricity may be desired to compensate for the fact that the distance from the image to the slit lamp pupil remains constant while the distance from the lens to the formed aerial image changes as front focal length is changed.

Figure 11:
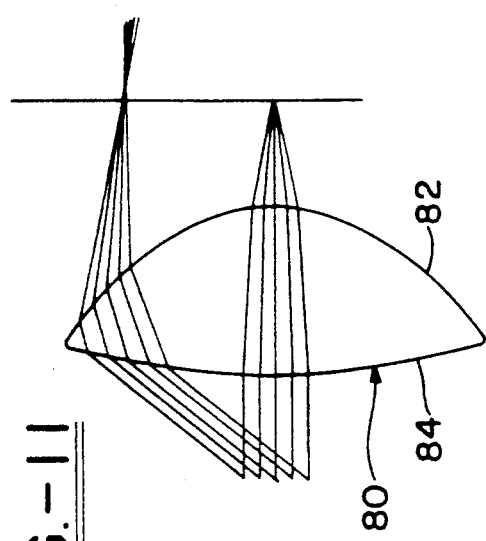
FIG. 11 shows a schematic representation of imaging characteristics for the example of an indirect ophthalmoscopy lens in accordance with the invention as shown in FIG. 10.
Figure 12:
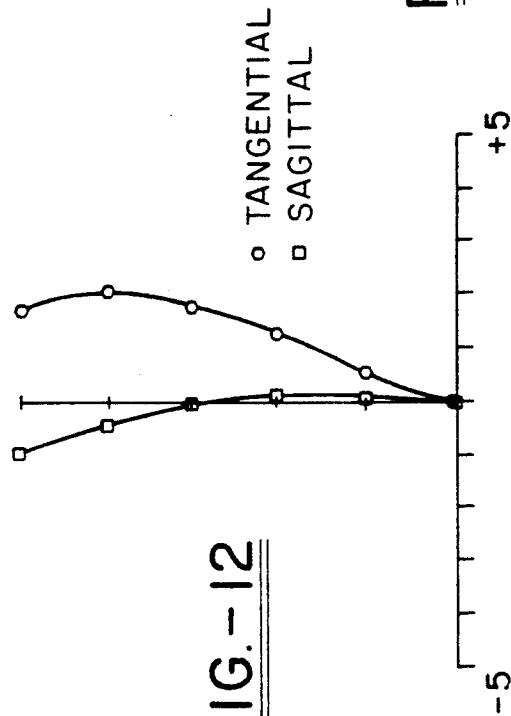
FIG. 12 shows the field curves for the indirect ophthalmoscopy lens in accordance with the invention, as shown in FIG. 10.

Turning now to FIGS. 10-12, another example of the indirect ophthalmoscopy lens in accordance with the invention is shown. In this example, the lens has a net power of approximately 110 diopters, with a 9.1 mm focal length and is designed to provide a field of view even greater than the previously described lens of FIGS. 4, 8 and 9. At this net power, the lens design also provides excellent pupil imagery as seen in FIG. 10. The lens (80) is made of an optical material having an index of refraction of 1.734, and has a thickness of 10.50 mm and diameter of 24.0 mm. The lens (80) has a first surface (82), having an apical radius of curvature, r, of 8.365 mm, and an apical eccentricity, e, of 1.0753. The second surface (84) has an apical radius of curvature 15.480 mm and an apical eccentricity of 5.547. For a 5 mm eye pupil, and a distance from the eye pupil to the lens of 5.91 mm, the imaging characteristics are shown to be relatively well corrected. Also, as shown in FIG. 12, the field curves for the lens of this example indicate that the lens is relatively well corrected for field aberrations, particularly with respect to the sagittal field.

Figure 13:
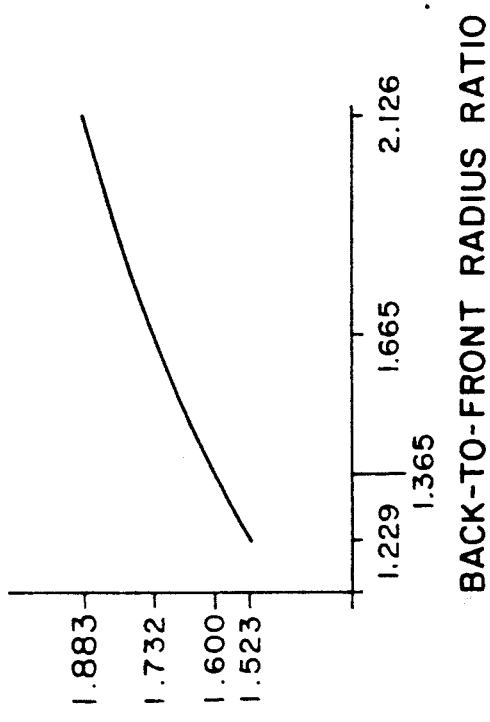
FIG. 13 shows a plot of the index of refraction of the indirect ophthalmoscopy lens of the invention versus the back to front radius ratio of the lens surfaces.
Figure 14:
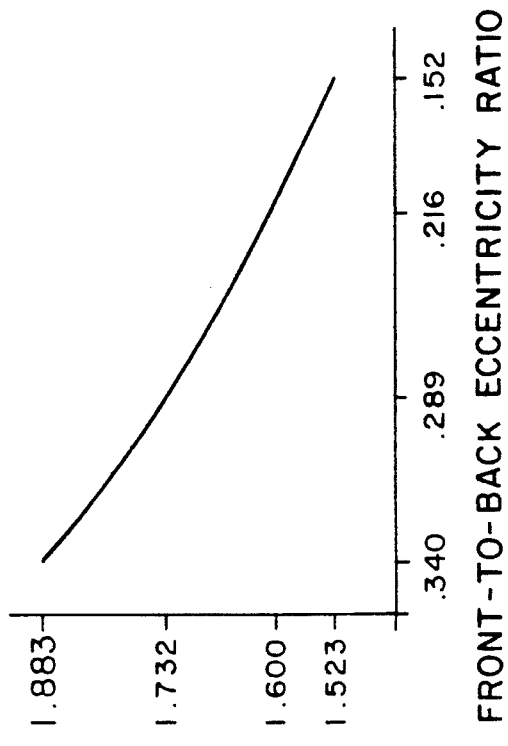
FIG. 14 shows a plot of the index of refraction of an indirect ophthalmoscopy lens in accordance with the invention versus the front to back eccentricity ratio of the surfaces.

Turning now to FIGS. 13 and 14, there are shown plots of the relationship of the index of refraction of the material from which the indirect ophthalmoscopy lens is made, relative to the back to front surface vertex radius ratios and the front to back surface apical eccentricity ratios for the lens design of the invention. In FIG. 13, there is seen a front to back surface power increase as index of refraction increases. Similarly, as seen in FIG. 14, the front to back eccentricity ratio decreases with increasing index of refraction, indicating a progressive increase in the back surface eccentricity as index of refraction increases. Various lens values have been calculated for representative cases of four different values of index of refraction. These values are based on lenses designed in accordance with the invention, all four designs having the same focal length, 12.68 mm, and with each lens corrected in an identical manner. The lens values include surface vertex radii, thickness, and front and back apical eccentricity. The lens diameter is 27 mm in each case, and the lens thicknesses were chosen to give approximately the same edge thickness at the outer rim of the lens. The lens designs are shown in Table I below:

TABLE I

|  | INDEX OF REFRACTION | | | |
| --- | --- | --- | --- | --- |
|  | n = 1.523 | n = 1.600 | n = 1.734 | n = 1.883 |
| Front Radius | 9.48 mm | 10.99 mm | 13.18 mm | 15.10 mm |
| Back Radius | 11.65 mm | 15.00 mm | 21.94 mm | 32.11 mm |
| Thickness | 13.00 mm | 11.50 mm | 9.53 mm | 8.25 mm |
| Front Eccentricity | 1.033 | 1.039 | 1.053 | 1.074 |
| Back Eccentricity | 3.039 | 3.590 | 4.864 | 7.087 |
| Ratio of Radii | 1.229 | 1.365 | 1.665 | 2.126 |

From the results as indicated in Table I, the front surface of the lens is seen to have an optimum eccentricity in the range from 1.0-1.1, which is almost independent of refractive index. The aerial image quality as well as the pupil imagery is identical in all four examples.

Based upon the foregoing, the relationships between the apical radii of curvature of the surfaces and the apical eccentricities provide the basis for optimal correction of both primary image quality and pupil aberrations. It has been found that if the at least one lens element is made from a material having an index of refraction in the range from 1.45 to 1.95, the ratio of the apical radius of curvature of the first and second surfaces may be in the range of 0.9 to 2.6, and the ratio of the apical eccentricity of the first and second surfaces may be in the range of 0.075 to 0.55, for lenses having a net power in the range of 50 to 150 diopters. Better correction of these aberrations is achieved by a ratio of the apical radius of curvature in the range from 1.2 to 2.3, and a ratio of the apical eccentricity in the range from 0.1 to 0.4. For a material having an index of refraction of approximately 1.523, the ratio of the apical radius of curvature of the first and second surfaces may be in the range of 0.9 to 1.8, and the ratio of the apical eccentricity of the first and second surfaces may be in the range of 0.15 to 0.55 for lenses having a net power of 50 to 150 diopters. Better correction of the field and pupil aberrations is achieved by a ratio of the apical radius of curvature in the range of 1.2 to 1.5, and a ratio of apical eccentricity in the range of 0.3 to 0.4. For a material having an index of refraction of approximately 1.60, the ratio of the apical radius of curvatures may be in the range of 1.0 to 1.9, and the ratio of the apical eccentricities may be in the range of 0.145 to 0.435 for lenses having a net power of 50 to 150 diopters. Better correction of these aberrations is achieved by a ratio of the apical radii of curvature in the range of 1.3 to 1.6, and a ratio of apical eccentricities in the range of 0.25 to 0.35. For a material having an index of refraction of approximately 1.734, the ratio of the apical radius of curvatures may be in the range of 1.3 to 2.2, and the ratio of the apical eccentricities may be in the range of 0.1 to 0.325 for lenses having a net power of 50 to 150 diopters.

Better correction of these aberrations is achieved by a ratio of the apical radii of curvature in the range of 1.6 to 1.9, and a ratio of apical eccentricities in the range of 0.15 to 0.25. For a material having an index of refraction of approximately 1.883, the ratio of the apical radius of curvatures may be in the range of 1.8 to 2.6, and the ratio of the apical eccentricities may be in the range of 0.075 to 0.25 for lenses having a net power of 50 to 150 diopters. Better correction of these aberrations is achieved by a ratio of the apical radii of curvature in the range of 2.0 to 2.3, and a ratio of apical eccentricities in the range of 0.1 to 0.2.

The novel indirect ophthalmoscopy lens for use with a slit lamp biomicroscope provides optimum image resolution as well as optimum pupil imagery and is particularly suited for use with a slit lamp biomicroscope. Although preferred embodiments of the invention have been described, it is to be understood that various modifications would be obvious to those skilled in the art, and are embodied within the present invention as defined by the appended claims.

What is claimed is:

1. An indirect ophthalmoscopy lens for use with a slit lamp or other biomicroscope in the examination of a patient's eye, comprising, at least one lens element having first and second convex aspheric surfaces of revolution, said first and second surfaces being coaxial and non-symmetrical with respect to one another, with the magnitude and shape of each of said first and second surfaces defined by the polynomial expressed as follows:

$$y=(2rx+(e^2-1)x^2)^{\frac{1}{2}}+Ax^F+Bx^G+Cx^H$$

where r equals the apical radius of curvature of each surface, e equals the apical eccentricity of each surface, and co-efficients A, B, and C equal successive terms in the polynomial, and F, G, and H equal exponents in the successive terms respectively, with the ratio of the apical radius of curvature and apical eccentricities of said first and second surfaces chosen to satisfy optical correction of image aberrations including curvature, astigmatism, and distortion while concomitantly satisfying optical correction for pupil aberrations, such that the chief rays emerging from a patient's eye which originate at the fundus of the eye and converge at the entrance pupil thereof will be conveyed by said at least one lens element to a focal area substantially coinciding with the pupil aperture of the objective lens system of the slit lamp or other biomicroscope.

2. The indirect ophthalmoscopy lens of claim 1, wherein, said at least one lens element is made from a homogenous transparent optical material having an index of refraction of approximately 1.523, with the ratio of the apical radii of respective curvatures of said first and second surfaces being in the range of 0.9 to 1.8, and the ratio of the respective apical eccentricities of said first and second surfaces being in the range of 0.15 to 0.55 for lenses having a net power of 50 to 150 diopters.

3. The indirect ophthalmoscopy lens of claim 2, wherein, said ratio of the apical radii of respective curvatures of said first and second surfaces is in the range of 1.2 to 1.5, and the ratio of the respective apical eccentricities is in the range of 0.3 to 0.4.

4. The indirect ophthalmoscopy lens of claim 1, wherein, said at least one lens element is made from a homogenous transparent optical material having an index of refraction of approximately 1.60, with the ratio of the apical radii of respective curvatures of said first and second surfaces being in the range of 1.0 to 1.9, and the ratio of the respective apical eccentricities of said first and second surfaces being in the range of 0.145 to 0.435 for lenses having a net power of 50 to 150 diopters.

5. The indirect ophthalmoscopy lens of claim 4, wherein, said ratio of the apical radii of respective curvatures of said first and second surfaces is in the range of 1.3 to 1.6, and the ratio of the respective apical eccentricities is in the range of 0.25 to 0.35.

6. The indirect ophthalmoscopy lens of claim 1, wherein, said at least one lens element is made from a homogenous transparent optical material having an index of refraction of approximately 1.734, with the ratio of the apical radii of respective curvatures of said first and second surfaces being in the range of 1.3 to 2.2, and the ratio of the respective apical eccentricities of said first and second surfaces being in the range of 0.1 to 0.325 for lenses having a net power of 50 to 150 diopters.

7. The indirect ophthalmoscopy lens of claim 6, wherein, said ratio of the apical radii of respective curvatures of said first and second surfaces is in the range of 1.6 to 1.9, and the ratio of the respective apical eccentricities is in the range of 0.15 to 0.25.

8. The indirect ophthalmoscopy lens of claim 1, wherein, said at least one lens element is made from a homogenous transparent optical material having an index of refraction of approximately 1.883, with the ratio of the apical radii of respective curvatures of said first and second surfaces being in the range of 1.8 to 2.6, and the ratio of the respective eccentricities of said first and second surfaces being in the range of 0.075 to 0.25 for lenses having a net power of 50 to 150 diopters.

9. The indirect ophthalmoscopy lens of claim 8, wherein, said ratio of the apical radii of respective curvatures of said first and second surfaces is in the range of 2.0 to 2.3, and the ratio of the respective apical eccentricities is in the range of 0.1 to 0.2.

10. The indirect ophthalmoscopy lens of claim 1, wherein, said at least one lens element is made from a homogenous transparent optical material having an index of refraction in the range from 1.45 to 1.95, with the ratio of the apical radii of respective curvatures of said first and second surfaces being in the range of 0.9 to 2.6, and the ratio of the respective apical eccentricities of said first and second surfaces being in the range of 0.075 to 0.55, for lenses having a net power in the range of 50 to 150 diopters.

11. The indirect ophthalmoscopy lens of claim 10, wherein, said ratio of the apical radii of respective curvatures is in the range from 1.2 to 2.3, and the ratio of the respective apical eccentricities is in the range from 0.1 to 0.4.

12. The indirect ophthalmoscopy lens of claim 1, wherein, said at least one lens element is made from a homogenous transparent optical material having an index of refraction of approximately 1.734, with said first surface having an apical radius of curvature, r, of approximately 13.18 mm, and an apical eccentricity, e, of approximately 1.053, with said second surface having an apical radius of curvature, r, of approximately 21.94 mm with an apical eccentricity, e, of 4.864, wherein the net power of the at least one lens element is approximately 79 diopters.

13. The indirect ophthalmoscopy lens of claim 1, wherein, said at least one lens element is made from a homogenous transparent optical material having an index of refraction of approximately 1.734, with said first surface having an apical radius of curvature, r, of approximately 8.365 mm, and an apical eccentricity, e, of approximately 1.075, with said second surface having an apical radius of curvature of approximately 15.48 mm and an apical eccentricity of approximately 5.547, wherein the net power of said at least one lens element is approximately 110 diopters.

14. The indirect ophthalmoscopy lens of claim 1, wherein, said at least one lens element includes a supporting housing to enable the lens to be held at a distance from the eye which corresponds to the back focal length of said at least one lens element.

15. The indirect ophthalmoscopy lens of claim 1, wherein, said first surface is a front surface of said at least one lens element and said second surface is a back surface of said at least one lens element, with the ratio of the apical radii of respective curvatures of said back and front surfaces being in the range of 0.9 to 2.6, and the ratio of the respective apical eccentricities of said front and back surfaces being in the range of 0.075 to 0.51 corresponding to the index of refraction of the material from which said at least one lens element is made, said index of refraction varying from 1.45 to 1.95 respectively.

16. The indirect ophthalmoscopy lens of claim 15, wherein, said front surface of said at least one lens element having an apical eccentricity in the range of 1.0 to 1.1, for a net power of said at least one lens element in the range between 50 to 150 diopters.

17. An indirect ophthalmoscopy lens for use with a slit lamp or other biomicroscope in the examination or treatment of a patient's eye, comprising, at least one lens element having first and second convex aspheric surfaces of revolution, said first and second surfaces being coaxial and non-symmetrical with respect to one another, with the magnitude and shape of each of said first and second surfaces defined by the polynomial expressed as follows:

$$y = (2rx + (e^2 - 1)x^2)^{\frac{1}{2}} + Ax^F + Bx^G + Cx^H$$

where r equals the apical radius of curvature of each surface, e equals the apical eccentricity of each surface, and co-efficients A, B, and C equal successive terms in the polynomial, and F, G, and H equal exponents in the successive terms respectively, with the ratio of the apical radii of respective curvatures and the ratio of respective apical eccentricities of said first and second surfaces being chosen to satisfy optical correction of pupil aberrations, satisfying optical correction such that the chief rays emerging from a patient's eye which originate at the fundus of the eye and converge at the entrance pupil thereof will be conveyed by said at least one lens element to a local area substantially coinciding with the pupil aperture of the objective lens system of the slit lamp or other biomicroscope.

18. The indirect ophthalmoscopy lens of claim 17, wherein,
said at least one lens element is made from a homogenous transparent optical material having an index of refraction in the range from 1.45 to 1.95, with the ratio of the apical radii of respective curvatures of said first and second surfaces being in the range of 0.9 to 2.6, and the ratio of the respective apical eccentricities of said first and second surfaces being in the range of 0.075 to 0.55, for lenses having a net power in the range of 50 to 150 diopters.

19. The indirect ophthalmoscopy lens of claim 17, wherein
said first surface is the front surface of said at least one lens element and said second surface is the back surface of said at least one lens element, with the ratio of the apical radius of curvature of said back surface to that of said front surface being in the range of 0.9 to 2.6, and the ratio of the apical eccentricity of said front surface to that of said back surface being in the range of 0.075 to 0.51 corresponding to the index of refraction of the material from which said at least one lens element is made, said index of refraction varying from 1.45 to 1.95 respectively.

* * * * *